United States Patent [19]
Vigil et al.

[11] Patent Number: 5,336,234
[45] Date of Patent: Aug. 9, 1994

[54] METHOD AND APPARATUS FOR DILATATION OF A STENOTIC VESSEL

[75] Inventors: Dennis Vigil, San Diego; Thomas E. Olson, Poway, both of Calif.

[73] Assignee: InterVentional Technologies, Inc., San Diego, Calif.

[21] Appl. No.: 58,406

[22] Filed: May 7, 1993

Related U.S. Application Data

[63] Continuation-in-part of Ser. No. 870,149, Apr. 17, 1992, Pat. No. 5,209,799.

[51] Int. Cl.$^5$ ............................................. A61M 25/10
[52] U.S. Cl. ................................... 606/159; 606/194; 606/171; 604/96
[58] Field of Search ............... 606/159, 169, 170, 171, 606/180, 192, 194; 604/96

[56] References Cited

U.S. PATENT DOCUMENTS

| | | | |
|---|---|---|---|
| Re. 32,983 | 7/1989 | Levy | 428/36.92 |
| Re. 33,561 | 3/1991 | Levy | 428/36.92 |
| 2,816,552 | 12/1957 | Hoffman | 606/170 |
| 3,749,085 | 7/1973 | Willson et al. | 606/159 |
| 4,140,126 | 2/1979 | Choudhury . | |
| 4,141,364 | 2/1979 | Schultze . | |
| 4,273,128 | 6/1981 | Lary . | |
| 4,292,974 | 10/1981 | Fogarty et al. . | |
| 4,406,656 | 9/1983 | Hattler et al. | 604/280 |
| 4,490,421 | 12/1984 | Levy . | |
| 4,608,984 | 9/1986 | Fogarty . | |
| 4,627,436 | 12/1986 | Leckrone . | |
| 4,685,458 | 8/1987 | Leckrone . | |
| 4,686,982 | 8/1987 | Nash . | |
| 4,705,517 | 11/1987 | DiPisa, Jr. | 623/12 |
| 4,723,549 | 2/1988 | Wholey et al. . | |
| 4,784,636 | 11/1988 | Rydell | 606/159 |
| 4,787,388 | 11/1988 | Hofmann . | |
| 4,936,845 | 6/1990 | Stevens | 606/159 |
| 5,042,985 | 8/1991 | Elliott et al. | 606/192 |
| 5,078,725 | 1/1992 | Enderle et al. | 606/193 |
| 5,085,662 | 2/1992 | Willard | 606/169 |
| 5,087,265 | 2/1992 | Summers | 606/159 |
| 5,100,425 | 3/1992 | Fischell et al. | 606/159 |
| 5,158,564 | 10/1992 | Schnepp | 606/169 |
| 5,176,693 | 1/1993 | Pannek, Jr. | 606/159 |
| 5,196,024 | 3/1993 | Barath | 606/192 |
| 5,209,799 | 5/1993 | Vigil | 606/170 |

FOREIGN PATENT DOCUMENTS

| | | | |
|---|---|---|---|
| 291170 | 11/1988 | European Pat. Off. | 606/159 |
| PCT/US90/-00337 | 1/1990 | European Pat. Off. . | |
| 9117714 | 11/1991 | PCT Int'l Appl. | 606/159 |

OTHER PUBLICATIONS

B. G. Lary, M.D., *Experimental Maintenance of Life by Intravenous Oxygen, Preliminary Report*, Clinical Congress of the American College of Surgeons, San Francisco, Nov. 5–9, 1951.

Banning G. Lary, M.D., *Effect of Endorcardial Incisions on Mycardial Blood Flow*, Archives of Surgery, Sep. 1963, vol. 87, pp. 424–427 (reprint).

Banning G. Lary, M.D., *Method for Increasing the Diameter of Long Segments of the Coronary Artery*, The American Surgeon, Jan., 1966, vol. 32, No. 1, pp. 33–35 (reprint).

Banning G. Lary, M.D.; John G. Chesney, M.D.; Thomas O. Gentsch, M.D., F.C.C.P. and Parry B. Larsen, M.D.; *The "Coronary Myocardial Artery" for Coronary Artery Disease*, Diseases of the Chest, vol. 29, No. 4, Apr., 1966, pp. 412–419 (reprint).

(List continued on next page.)

*Primary Examiner*—Ralph Lewis
*Attorney, Agent, or Firm*—Nydegger & Associates

[57] ABSTRACT

An apparatus and method of operation are disclosed for using an expandable balloon catheter to perform a combination angioplasty and atherectomy procedure on a stenotic blood vessel. The expandable balloon has a plurality of atherotomes attached to its outer surface, and longitudinal, transverse, or rotational oscillatory motion is imparted to the atherotomes to assist in incising the stenotic tissue, prior to or during dilatation of the stenotic segment of the blood vessel.

7 Claims, 3 Drawing Sheets

OTHER PUBLICATIONS

Banning G. Lary, M.D., *Onlay Vein Grant for the Correction of Coronary Artery Obstruction,* Surgery, vol. 59, No. 4, pp. 547–551, Apr., 1966 (reprint).

Banning G. Lary, M.D. and Roger W. Sherman, M.D., *A Method for Creating a Coronary–Myocardial Artery,* Surgery, vol. 59, No. 6, pp. 1061–1064, Jun., 1966.

Banning G. Lary, M.D., *A Method to Create and Correct Stenosis of a Coronary Artery,* Archives of Surgery, vol. 93, pp. 828–830, Nov. 1966.

Banning G. Lary, M.D., *An Epicardial Purse String Suture for Closing Coronary Arteriotomy,* The American Surgeon, No. 3, pp. 213–214, Mar., 1967.

Banning G. Lary, M.D., *Surgery for Coronary Artery Disease,* Nursing Clinics of North American, vol. 2, No. 3, pp. 537–542, Sep., 1967.

Banning G. Lary, M.D.,; Antonio Camelo, M.D.; Roger W. Sherman, M.D.; and Thomas J. Noto, M.D., *Myocardial Revascularization Experiments Using the Epicardium,* Archives of Surgery, vol. 98, pp. 69–72, Jan., 1969.

Banning G. Lary, M.D., *Coronary Artery Resection and Replacement by a Blood Conduit,* Surgery, vol. 65, No. 4, pp. 584–589, Apr., 1969.

Banning G. Lary, M. D.; Roger W. Sherman, M.D.; Sonya S. Glasser; Joan McDermott; and Frank Gollan, M.D., *Experimental Vein Angioplasty of the Circumflex Coronary Artery,* Journal of Surgical Research, vol. 17, pp. 210–214, 1974.

Banning G. Lary, M.D., *Coronary Artery Incision and Dilation,* Archives of Surgery, vol. 115, pp. 1478–1480, Dec., 1980.

METHOD AND APPARATUS FOR DILATATION OF A STENOTIC VESSEL

This application is a continuation-in-part of application Ser. No. 07/870,149, filed Apr. 17, 1992 now U.S. Pat. No. 5,209,799.

TECHNICAL FIELD

The present invention relates generally to devices which dilate a blood vessel across a stenotic segment of the vessel. In particular, the present invention relates to a method and apparatus for the dilatation of a stenotic segment of a blood vessel using a combination device for compression and incision of the stenosis. More particularly, this invention relates to a method and apparatus employing a folding balloon catheter having oscillatable atherotomes mounted along the outer surface of the balloon or the catheter.

BACKGROUND OF THE INVENTION

Blockage of human arteries is a widespread malady and, as such, represents a significant health concern. Blockages reducing blood flow through the coronary arteries to the heart can cause heart attacks, while blockages reducing blood flow through the arteries to the brain can cause strokes. Similarly, arterial blockages reducing blood flow through arteries to other parts of the body can produce grave consequences in an affected organ or limb.

The build-up of atherosclerotic plaque is a chief cause of blockages, termed stenoses, which reduce blood flow through the arteries. Consequently, several methods have been introduced to alleviate the effects of plaque build-up in restricting the artery. One such method is a procedure termed angioplasty, which uses an inflatable device positioned at the stenosis to dilate the artery. A typical angioplasty device is disclosed in U.S. Pat. No. 4,896,669 to Bhate et al. The angioplasty device of Bhate et al. includes an inflatable balloon which is attached to the distal end of a hollow catheter tube. The proximal end of the catheter tube is attached to a fluid source.

To treat an arterial stenosis, the balloon of Bhate et al. is introduced into the artery in a deflated state and guided through the artery over a guide wire to a position adjacent the stenosis. Fluid from the fluid source is then infused into the balloon via the catheter tube to inflate the balloon. As the balloon expands, it presses against the arterial wall in the region of the stenosis, dilating the artery at the stenosis and restoring it to a sufficient size for adequate blood flow therethrough. The balloon is then deflated and removed from the artery, thereby completing the treatment. Sometimes, the effectiveness of this treatment is limited, because the stenotic tissue is left essentially intact.

Another method is disclosed in U.S. Pat. No. 4,273,128 to Lary. In the Lary method, a combination balloon and surgical knife assembly is inserted into the blood vessel and advanced to the stenosis. The knife blade is then forced through the stenotic tissue, followed by expansion and advancement of the balloon to dilate the vessel. As this method involves advancement of a sharp surgical blade through the vessel, care must be taken to avoid damage to vessel walls or perforation of the epicardium.

It has been found that dilatation of the stenotic segment of a blood vessel is facilitated by incision of the stenotic tissue, either before or during expansion of the dilating balloon. The methods heretofore known fail to perform this function without some serious drawbacks. Therefore, it is an object of the present invention to provide a method and apparatus for dilatation of a stenotic segment using a combination balloon and cutting device which has minimal risk of damaging surrounding tissues. It is also an object of the present invention to provide a method and apparatus for dilatation of a stenotic segment using oscillatory motion to assist in incision of the stenotic tissue before dilatation of the segment. It is a further object of the present invention to provide a method and apparatus for dilatation of a stenotic segment using oscillatory motion to assist in incision of the stenotic tissue during dilatation of the segment. Still another object of this invention is to provide an effective apparatus for dilatation of a stenotic segment using oscillatory motion, which is relatively inexpensive to manufacture and easy to operate.

SUMMARY OF THE INVENTION

The present invention is an apparatus, and a method for using the apparatus, consisting of an expandable balloon catheter which includes a plurality of elongated atherotomes that are attached to the outer surface of the catheter, either on the balloon, or elsewhere on the catheter assembly. The device is useful in an angioplasty procedure to incise stenotic tissue in a blood vessel, and to thereby facilitate dilatation of the vessel as the balloon is expanded.

The atherotomes can have a variety of shapes, but they will preferably be elongated, with a triangular cross section, and with an outwardly facing cutting edge at the apex of the triangle. The cutting action is assisted by imparting an oscillatory motion to the atherotomes, either directly or through the balloon. The method of use of the catheter assembly can involve use of the oscillatory motion either before or during the dilatation of the blood vessel. The mode of the oscillatory motion can be longitudinal along the axis of the catheter, transverse to the axis, rotational about the axis, or a combination of two or more of these modes. Imposition of the oscillatory motion can be through the catheter tube, through an additional mechanical connection, or through a fluid within the catheter.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF PREFERRED EMBODIMENTS

Figure 1:
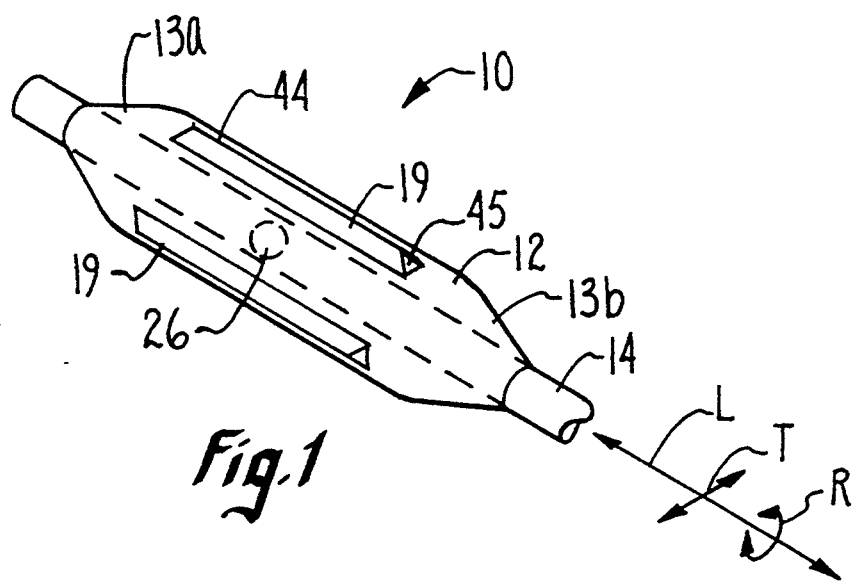
FIG. 1 is a perspective view of an expanding balloon catheter of the present invention, in the expanded condition.
Figure 3:
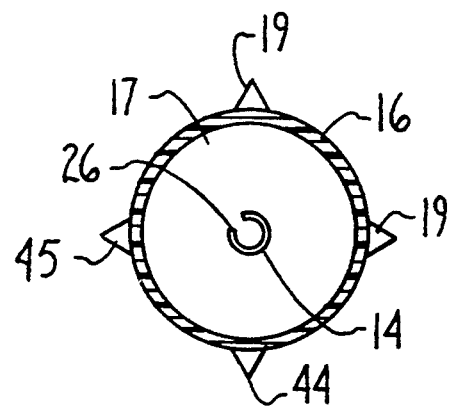
FIG. 3 is a sectional view of the expanding balloon catheter of FIG. 1, showing the balloon in the expanded condition.

The present invention is an apparatus for the use of oscillatory motion to assist in the dilatation of a stenotic segment of a blood vessel, and a method of performing the procedure with this apparatus. The apparatus of the present invention includes a folding balloon catheter, such as the balloon catheter disclosed in application Ser. No. 07/870,149, filed Apr. 17, 1992, which has been allowed, and which is incorporated herein by reference. Such a balloon catheter is shown in FIG. 1 and generally designated 10. In accordance with the present invention, a conventional angioplasty balloon 12 is joined with a hollow catheter tube 14. The balloon 12 is preferably shaped as a hollow tubular structure having a thin outer wall 16. As seen in FIG. 1, the ends 13a and 3b of balloon 12 are tapered inwardly. Preferably, the wall 16 of balloon 12 is made of a pliant polymeric material which encloses and defines an interior chamber 17 which is best seen in FIG. 3. Preferably balloon 12 is made of a material well know in the art, such as a biaxially oriented material. The catheter tube 14 is flexible and, like balloon 12, is preferably formed from a polymeric material. Additionally, catheter tube 14 has a port 26 that is positioned near one end of the tube 14.

In order to join the balloon 12 to catheter tube 14, the tube 14 is inserted into balloon 12 to extend through the chamber 17. The ends 13a and 13b of balloon 12 are then sealed to catheter tube 14. Consequently, any fluid communication with the chamber 17 can only be accomplished from catheter tube 14 through the port 26. The seal between ends 13a and 13b of balloon 12 and catheter tube 14 is effected by any known bonding. The result is a balloon catheter structure which is further modified according to the following description.

With the balloon 12 attached to catheter tube 14, the balloon 12 is inflated. This is done by infusing a fluid such as air into the balloon chamber 17, under pressure, which causes the balloon chamber 17 to expand. When balloon 12 is inflated, wall 16 defines a substantially cylindrical surface having tapered ends. At least one cutting element or atherotome 19 is mounted onto the outer surface of balloon 12, such as by the use of adhesive. Four atherotomes 19 are mounted onto the balloon 12 in the embodiment shown, but the number of atherotomes used can be one or more, as desired, without departing from the invention.

Figure 2:
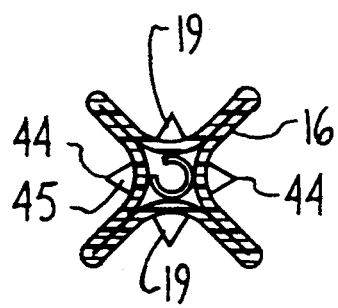
FIG. 2 is a sectional view of the expanding balloon catheter of FIG. 1, showing the balloon in the collapsed condition.

Atherotome 19 can have a variety of shapes and sizes and still function in accordance with the present invention, but the preferred embodiment is shown in FIGS. 1 through 3 to be an elongated cutter with a triangular cross section. At the apex of the triangular section is cutting edge 44. Since the method of the present invention imparts an oscillatory motion to the atherotome 19, it is capable of cutting into stenotic tissue with its triangular, or wedge, shape, and cutting edge 44. As can be seen, the ends 45 of atherotome 19 are sloped to facilitate insertion of atherotome 19 into the stenotic tissue. As shown in FIG. 2, balloon 12 will typically form alternating flaps and furrows when it is collapsed, and atherotomes 19 are placed in such furrows. This placement can serve to protect blood vessel walls from damage by atherotomes 19 during advancement of catheter 10 through a blood vessel to a stenotic segment.

Also shown in FIG. 1 are the three modes of oscillatory motion contemplated in the method of the present invention. Longitudinal motion L oscillates along the longitudinal axis of catheter 10, transverse motion T oscillates at right angles to the longitudinal axis of catheter 10, and angular or rotational motion R oscillates about the longitudinal axis of catheter 10. The choice of oscillatory mode will depend upon such things as the particular embodiment of catheter 10 used, the particular embodiment of atherotome 19 used, and physiological factors present in a given application. The oscillatory motion used can also have a combination of any two or more of the three directional modes discussed.

In the embodiment shown in FIG. 1, the oscillatory motion will be imparted indirectly to the atherotomes 19 via catheter tube 14 and balloon 12, or directly to the atherotomes 19. The indirect method would be accomplished by means of longitudinal or transverse vibration or rotational oscillation of catheter tube 14 by an electromagnetic vibrating device, shown as vibrator 50 in FIGS. 6 and 7, similar to one disclosed in application Ser. No. 07/944,473, filed Sep. 14, 1992, incorporated herein by reference, or by another vibrating device of the types that are known in the art. Vibrator 50 has a power source, control circuits, and vibrating motor (not shown) housed in case 52, and a clamp 54 attached to the vibrating motor. The motion of clamp 54 is longitudinal, controlled by a longitudinally oriented track in housing 52, in the above incorporated application. It could be converted to transverse or rotational oscillatory motion., as desired, by the use of a transversely oriented track or by the use of oscillating linkages as are known in the art.

The direct method of imparting oscillatory motion to the embodiment shown in FIG. 1 could be to impart translational motion to atherotomes 19 by means of generating pulses in a fluid within catheter tube 14 and chamber 17 with a fluid pulse generating device (not shown) of the types that are known in the art.

Figure 4:
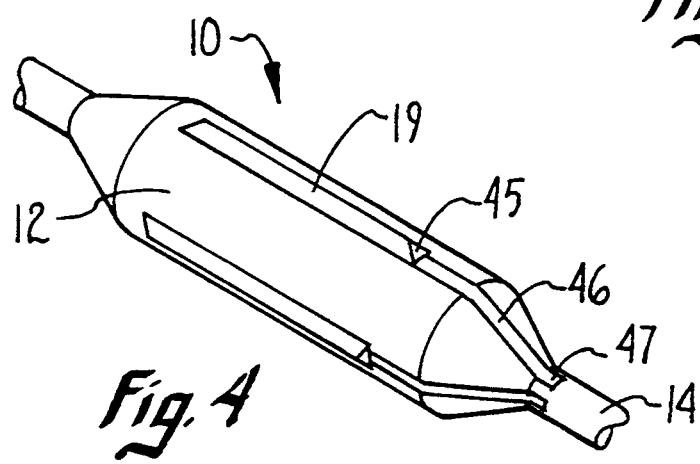
FIG. 4 is a perspective view of an alternate embodiment of an expanding balloon catheter of the present invention.

As seen in FIG. 4, a catheter 10 of the present invention can have atherotomes 19 mechanically attached by strips 46 to catheter tube 14. Strips 46 are shown attached to one end 45 of atherotome 19 and to the outer surface of catheter tube 14 at connection point 47. Strips 46 can be flat strips of metal or a stiff plastic, as desired, and they can be welded or bonded to atherotome 19 and to catheter tube 14, depending upon the materials of construction. Strips 46 can also be bonded to balloon 12 or separate therefrom. This alternate embodiment of balloon 12 uses strips 46 to attach atherotomes 19 to catheter tube 14 for the applications where it is desirable to impart oscillatory motion to atherotomes 19 without relying on the stiffness of thin outer wall 16 of balloon 12. Such applications might be where the stenotic tissue is particularly tough, or where the opening through the stenosis is particularly small, requiring the imposition of more force or higher frequencies in the oscillatory motion of atherotomes 19 than is possible in view of the dampening effect of thin wall 16. The oscillatory motion can be received via catheter tube 14, as shown, or it could easily be transmitted independently of catheter tube 14 via a wire (not shown) or other stiff member either inside or outside of catheter tube 14. For instance, a guide wire as is known in the angioplasty art could be adapted for this purpose. Regardless of the means of transmitting the oscillatory motion to the atherotomes 19 in FIG. 4, this motion could be longitudinal, transverse, or rotational, as desired.

Figure 5:
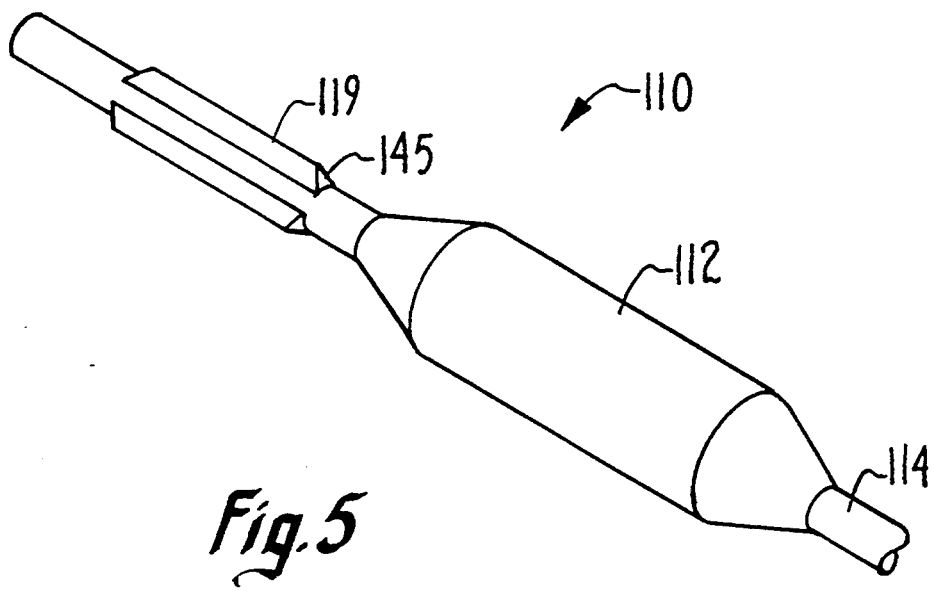
FIG. 5 is a perspective view of a second alternate embodiment of an expanding balloon catheter of the present invention.

A second alternate embodiment of the apparatus of the present invention is seen in FIG. 5, where the catheter 110 has atherotomes 119 attached directly to catheter tube 114, immediately adjacent to balloon 112. Atherotomes 119 are elongated, with triangular cross-sections, and with sloped ends 145. They can be of sufficient height to extend radially outwardly from catheter tube 114 a sufficient distance to incise deeply enough into stenotic tissue to facilitate the passage of balloon 112. In this embodiment, oscillatory motion would be imparted indirectly to atherotomes 119 via catheter tube 114, by longitudinal, transverse, or rotational oscillation of catheter tube 114 as hereinbefore discussed. In the alternative, oscillatory motion can be applied directly to atherotomes 119 via a wire, as discussed above, if atherotomes are resiliently mounted to catheter tube 114, such as by use of a resilient adhesive.

OPERATION

Figure 6:
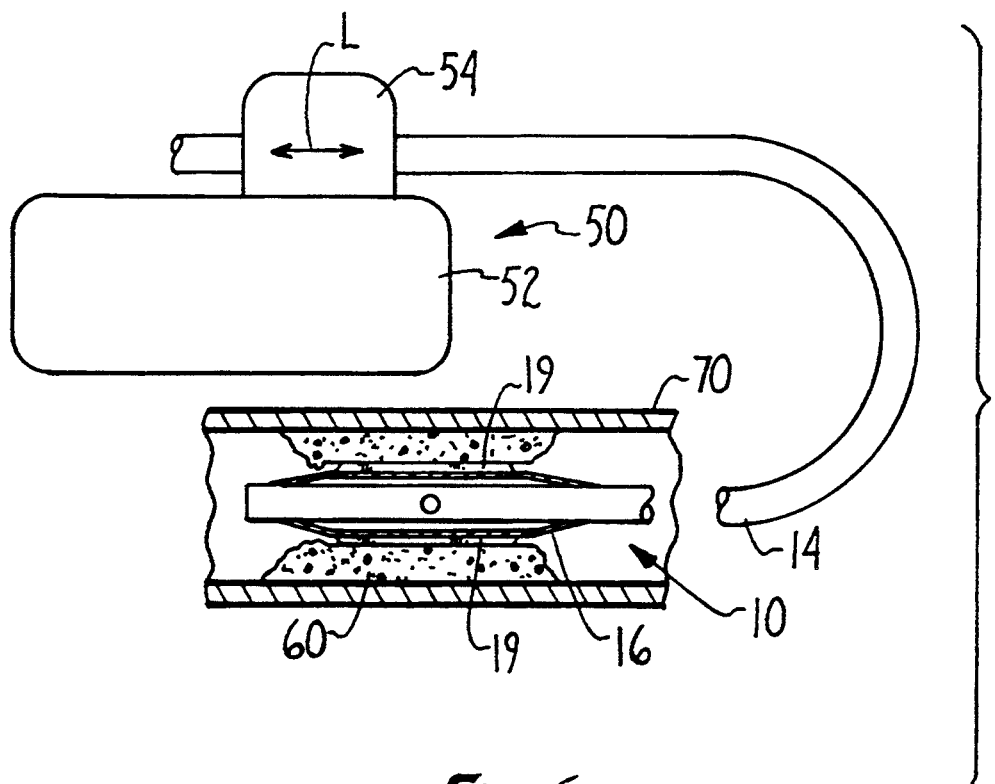
FIG. 6 is a sectional view of the expanding balloon catheter of FIG. 1, showing the balloon in the collapsed condition and inserted into a stenotic segment of a blood vessel.
Figure 7:
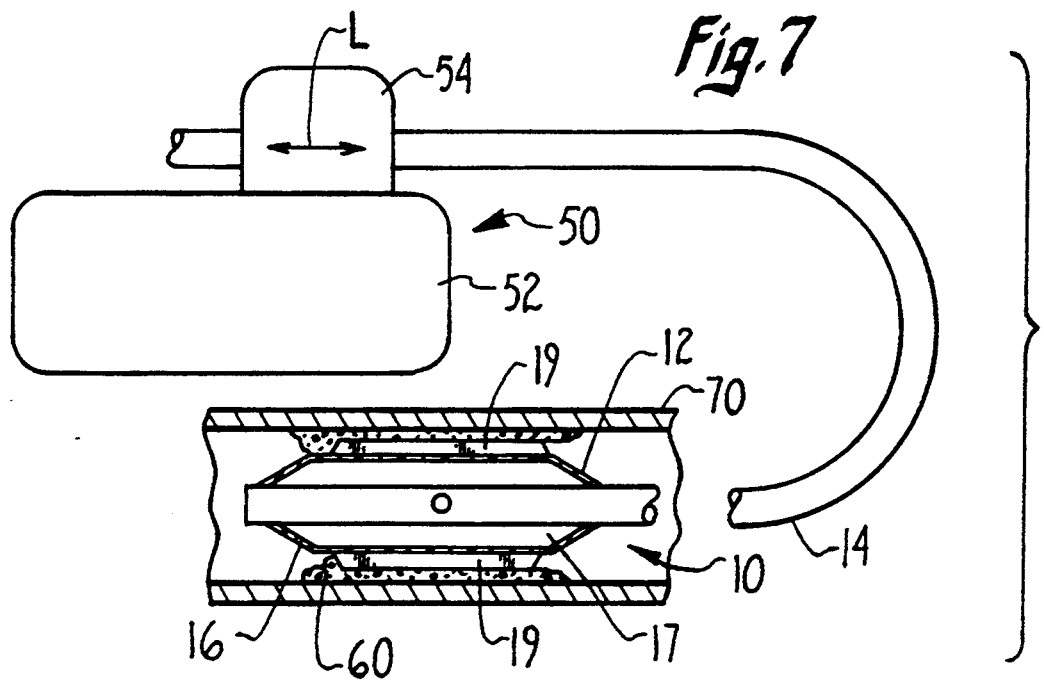
FIG. 7 is a sectional view of the expanding balloon catheter of FIG. 1, showing the balloon in the expanded condition after dilatation of a stenotic segment of a blood vessel.

Operation of the apparatus of the present invention can be understood by reference to FIGS. 6 and 7, where balloon 12 is shown mounted on catheter tube 14, and atherotomes 19 are shown mounted on balloon 12 as in the embodiment shown in FIG. 1. Catheter 10 is inserted, by known methods, into blood vessel 70 and advanced to stenotic tissue 60, with balloon 12 collapsed. Catheter 10 is then further advanced to position balloon 12 and atherotomes 19 into the stenotic segment. If stenosis is sufficiently severe, vibrator 50 can be energized to impart longitudinal, transverse, or rotational oscillations to atherotomes 19 via catheter tube 14 and balloon 12, to incise stenotic tissue 60 and aid in advancement of balloon 12 into the stenotic segment.

When balloon 12 has been advanced into the stenotic segment, vibrator 50 is energized to impart longitudinal, transverse, or rotational oscillations to atherotomes 19, as desired, and fluid pressure is simultaneously increased in catheter tube 14 and interior chamber 17, to expand balloon 12 to dilate the stenotic segment as shown in FIG. 7. Fluid pressure can be provided via catheter tube 14 by means (not shown) that are well known in the angioplasty art. If oscillatory motion is to be applied to atherotomes 19 via a separate wire as discussed above, the separate wire would be clamped in clamp 54 of vibrator 50, rather than catheter tube 14 as shown in FIGS. 6 and 7. After dilatation, fluid pressure can be reduced to collapse balloon 12, facilitating its removal from blood vessel 70.

Figure 8:
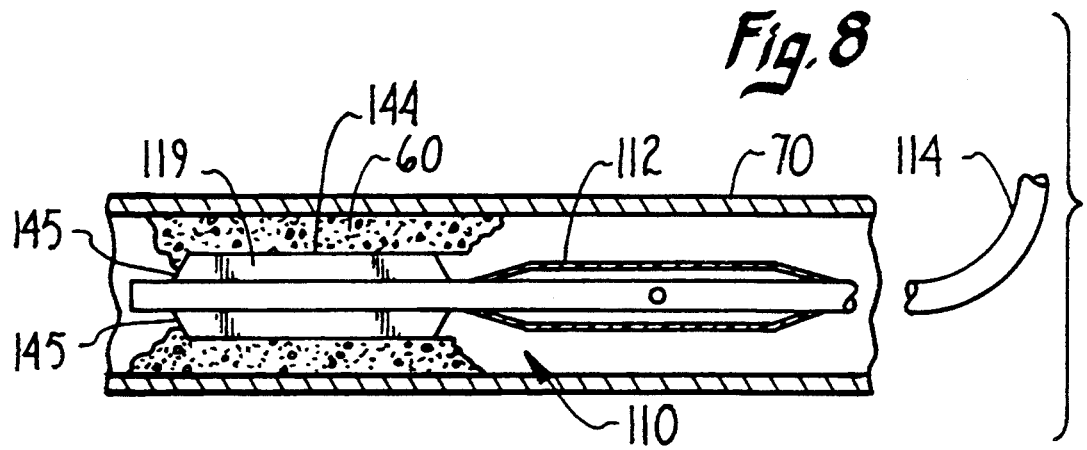
FIG. 8 is a sectional view of the expanding balloon catheter of FIG. 5, showing the atherotomes inserted into a stenotic segment of a blood vessel, and showing the balloon in the collapsed condition.
Figure 9:
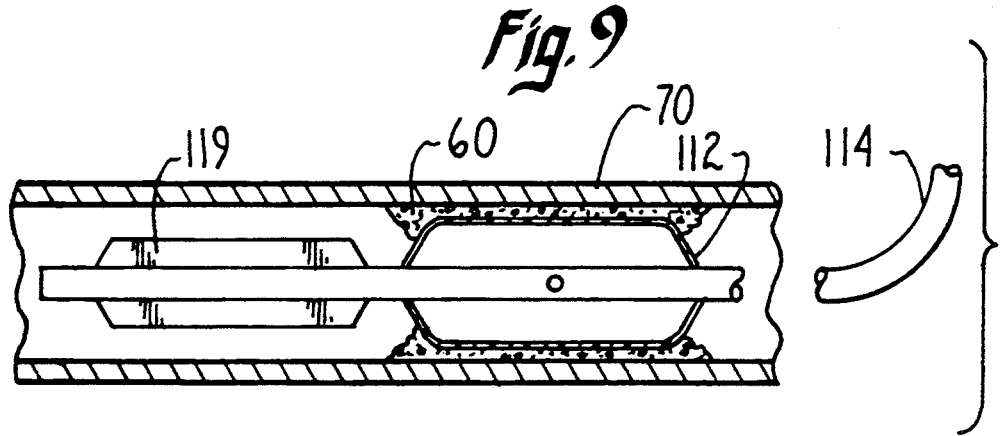
FIG. 9 is a sectional view of the expanding balloon catheter of FIG. 5, showing the balloon after advancement into the stenotic segment and after expansion of the balloon to dilate the stenotic segment.

Operation of another embodiment of the apparatus of the present invention is shown in FIGS. 8 and 9, where, as in FIG. 5, atherotomes 119 are shown attached directly to catheter tube 114 adjacent to balloon 112. In FIG. 8, catheter 110 has been inserted by known methods into blood vessel 70 and advanced to a stenotic segment, with balloon 112 in the collapsed condition.

Still in FIG. 8, catheter 110 has been further advanced until atherotomes 119 have incised stenotic tissue 60. Incision of stenotic tissue 60 is assisted by energization of vibrator 50 as described before, and imposition of longitudinal, transverse, or rotational oscillations on atherotomes 119 via catheter tube 114, as atherotomes 119 are advanced into stenotic tissue 60. This incision step is also assisted by sloped ends 145, or other suitable cutting contours, on atherotomes 119.

After the incision step, catheter 110 is further advanced, with balloon 112 still in the collapsed condition, until balloon 112 is aligned with the stenotic segment of blood vessel 70. As shown in FIG. 9, fluid pressure is then applied to catheter 114 by means known in the angioplasty art, and balloon 112 is expanded to dilate the stenotic segment.

While the particular method and apparatus for dilatation of a stenotic vessel as herein shown and disclosed in detail are fully capable of obtaining the objects and providing the advantages hereinbefore stated, it is to be understood that they are merely illustrative of the presently preferred embodiments of the invention and that no limitations are intended to the details of operation, construction or design herein shown other than as described in the appended claims.

I claim:

1. An expanding balloon catheter dilatation system using oscillatory motion, for dilating a stenotic blood vessel, comprising:
   a balloon enclosing an expandable chamber;
   a hollow catheter tube attached to said balloon in fluid communication with said chamber;
   at least one atherotome mounted on the exterior surface of said balloon; and
   an oscillatory device mechanically linked to said at least one atherotome for imparting oscillatory motion to said at least one atherotome.

2. An expanding balloon catheter dilatation system as claimed in claim 1, wherein said oscillatory device is directly linked to said catheter tube and thereby mechanically linked via said balloon to said at least one atherotome.

3. An expanding balloon catheter dilatation system as claimed in claim 1, further comprising at least one oscillation transmitting strip linking said catheter tube to said at least one atherotome, wherein said oscillatory device is directly linked to said catheter tube and thereby mechanically linked via said at least one oscillation transmitting strip to said at least one atherotome.

4. An expanding balloon catheter dilatation system as claimed in claim 1, wherein said at least one atherotome has an elongated cutting edge parallel to, and directed radially outwardly from, the longitudinal axis of said catheter tube.

5. An expanding balloon catheter dilatation system as claimed in claim 1, wherein said oscillatory device comprises an electromagnetic vibrator capable of creating longitudinal physical oscillations of said catheter tube.

6. An expanding balloon catheter dilatation system using oscillatory motion, for dilating a stenotic blood vessel, comprising:
   an elongated balloon enclosing an expandable chamber;
   a hollow catheter tube attached to said balloon in fluid communication with said chamber;
   a plurality of elongated atherotomes mounted externally on said balloon, parallel to the longitudinal axis of said balloon, with the cutting edges of said atherotomes directed radially outwardly from said longitudinal axis; and a vibrator mechanically linked to said catheter tube for imparting longitudinal oscillatory motion to said plurality of atherotomes via said balloon and via said catheter tube.

7. A method for dilatation of a stenotic blood vessel, comprising the steps of:

mounting an expandable balloon on a hollow catheter tube, to form a catheter assembly;

mounting at least one atherotome on an exterior surface of said balloon;

attaching said catheter tube to a vibrator capable of producing longitudinal vibrations;

inserting said catheter assembly into a blood vessel;

advancing said balloon and said at least one atherotome to a stenosis in the blood vessel; and simultaneously imparting longitudinal vibrations to said at least one atherotome via said catheter tube and via said balloon to incise said stenosis and expanding said balloon to dilate the blood vessel.

* * * * *